United States Patent
Josyula et al.

(10) Patent No.: US 7,435,751 B2
(45) Date of Patent: Oct. 14, 2008

(54) 7-FLUORO-1,3-DIHYDRO-INDOL-2-ONE OXAZOLIDINONES AS ANTIBACTERIAL AGENTS

(76) Inventors: Vara Prasad Venkata Nagendra Josyula, 3302 Woodhill Cir., Superior Township, MI (US) 48198; Mikhail Gordeev, 5072 Stone Canyon Dr., Castro Valley, CA (US) 94552; Gary Luehr, 28570 Fox Hollow Dr., Hayward, CA (US) 94542

(*) Notice: Subject to any disclaimer, the term of this patent is extended or adjusted under 35 U.S.C. 154(b) by 36 days.

(21) Appl. No.: 11/393,961

(22) Filed: Mar. 30, 2006

(65) Prior Publication Data

US 2006/0229349 A1  Oct. 12, 2006

Related U.S. Application Data

(60) Provisional application No. 60/668,715, filed on Apr. 6, 2005, provisional application No. 60/684,033, filed on May 24, 2005.

(51) Int. Cl.
*A61K 31/421* (2006.01)
*A61K 31/422* (2006.01)
*C07D 263/04* (2006.01)
*C07D 413/04* (2006.01)

(52) U.S. Cl. ............... 514/376; 548/215; 548/225; 548/229; 514/374

(58) Field of Classification Search ............... 548/215, 548/225, 229; 514/374, 376
See application file for complete search history.

(56) References Cited

U.S. PATENT DOCUMENTS

| 5,164,510 | A | 11/1992 | Brickner | 548/231 |
| 6,417,403 | B1 | 7/2002 | Roh et al. | 564/468 |
| 7,012,088 | B2 * | 3/2006 | Poel | 514/376 |
| 2006/0030609 | A1 | 2/2006 | Luehr et al. | 514/376 |

FOREIGN PATENT DOCUMENTS

| DE | 19604223 | 8/1997 |
| DE | 19649095 | 8/1997 |
| EP | 693491 | 1/1996 |
| EP | 694543 | 1/1996 |
| EP | 609905 | 6/2001 |
| WO | WO99/37630 | 7/1999 |
| WO | WO99/52855 | 10/1999 |
| WO | WO00/29396 | 5/2000 |
| WO | WO00/32599 | 6/2000 |
| WO | WO00/73301 | 12/2000 |
| WO | WO02/32857 | 4/2002 |
| WO | WO02/81470 | 10/2002 |
| WO | WO02/85849 | 10/2002 |
| WO | WO03/072553 | 9/2003 |
| WO | WO2004/0074282 | 9/2004 |
| WO | WO2006/0016220 | 2/2006 |

* cited by examiner

*Primary Examiner*—Golam M Shameem
(74) *Attorney, Agent, or Firm*—Steve T. Zelson; Christian M. Smolizza

(57) ABSTRACT

The present invention provides a compound of formula I

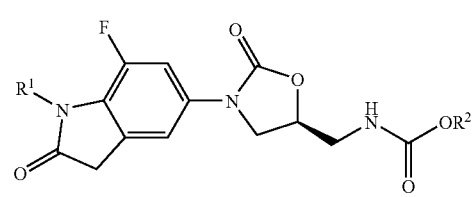

or a pharmaceutically acceptable salt thereof wherein $R^1$ is $C_{1-4}$alkyl, optionally substituted with a fluoro atom, or $R^1$ is a cyclopropyl or cyclopropylmethyl; and $R^2$ is methyl or ethyl. These compounds are useful as antibacterial agents.

19 Claims, No Drawings

7-FLUORO-1,3-DIHYDRO-INDOL-2-ONE OXAZOLIDINONES AS ANTIBACTERIAL AGENTS

CROSS REFERENCE TO RELATED APPLICATIONS

The present application claims the benefit of U.S. Provisional Patent Application No. 60/668,715 filed on Apr. 6, 2005, and U.S. Provisional Patent Application No. 60/684,033 filed on May 24, 2005, the disclosures of which are incorporated herein by reference in their entirety.

FIELD OF INVENTION

The present invention relates to 7-fluoro-1,3-dihydro-indol-2-one oxazolidinone derivatives, their use as antibacterial agent, to pharmaceutical compositions containing these compounds and to methods for their preparations.

BACKGROUND OF THE INVENTION

Antibacterial resistance is a global clinical and public health problem that has emerged with alarming rapidity in recent years and undoubtedly will increase in the near future. Resistance is a problem in the community as well as in health care settings, where transmission of bacteria is greatly amplified. Because multiple drug resistance is a growing problem, physicians are now confronted with infections for which there is no effective therapy. As result, structurally novel antibacterials with a new mode of action have become increasingly important in the treatment of bacterial infections.

Among newer antibacterial agents, oxazolidinone compounds are the most recent synthetic class of antimicrobials. This invention provides 7-fluoro-1,3-dihydro-indol-2-one oxazolidinone derivatives as inhibitors of bacterial protein synthesis for the treatment of serious infections caused by a number of human and veterinary pathogens, including multiple resistant strains of bacteria.

INFORMATION DISCLOSURE

WO 2003072553 discloses N-aryl-2-oxazolidinone-5-carboxamides having antibacterial activity useful for treating microbial infections. WO 200281470 discloses oxazolidinone compounds useful for treating bacterial infection. WO 200073301 discloses bicyclic oxazolidinone derivatives useful as antimicrobial agents. WO 200032599 discloses oxazolidinone derivatives useful for treatment of microbial infections. WO 200029396 discloses 3-phenyl-5-aminomethyl-oxazolidinone derivatives useful as antibacterial agents. WO 9937630 discloses oxazolidinone derivatives including combinatorial libraries. DE 19604223 discloses new substituted oxazolidinone compounds useful as antibacterial agents. DE 19649095 discloses 5-(acyl-aminomethyl)-3-hetero-aryl-oxazolidinone compounds useful as antibacterial agents. EP 694543 discloses hetero-aryl substd. oxazolidinone derivatives useful as antibacterial agents. EP 693491 discloses 3-hetero-aryl-2-oxazolidinone derivatives useful as antibacterial agents. EP 609905 discloses indazolyl, benzimidazolyl, and benzofrizxolyl oxazolidinone derivatives useful as antibacterial agents. U.S. Pat. No. 5,164,510 discloses 5-Indolinylioxazolidin-2-one(s) useful as antibacterial agents. WO 04/074282 discloses indoline oxazolidinones and derivatives thereof. U.S. provisional patent application 60/599,822 discloses oxazolidinones containing oxindoles as antibacterial agents.

SUMMARY OF THE INVENTION

The present invention provides a compound of formula I

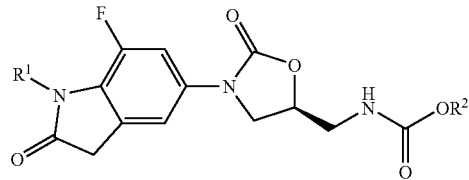

or a pharmaceutically acceptable salt thereof wherein $R^1$ is $C_{1-4}$alkyl, optionally substituted with a fluoro atom, or $R^1$ is a cyclopropyl or cyclopropylmethyl; and $R^2$ is methyl or ethyl.

In another aspect, the present invention also provides: pharmaceutical compositions which comprise a pharmaceutically acceptable carrier and a compound of formula I, methods for treating microbial infections in a mammal by administering to a mammal in need a therapeutically effective amount of a compound of formula I, or a pharmaceutically acceptable salt thereof, and a use of a compound of formula I or a pharmaceutically acceptable salt thereof to prepare a medicament for treating microbial infections.

DETAILED DESCRIPTION OF THE INVENTION

Unless otherwise stated, the following terms used in the specification and claims have the meanings given below:

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to seven carbon atoms, inclusive.

The term alkyl refers to both straight and branched groups, but reference to an individual radical such as "propyl" embraces only the straight chain radical, a branched chain isomer such as "isopropyl" being specifically referred to.

The term "$C_{3-5}$cycloalkyl" refers to a cyclic saturated monovalent hydrocarbon group of three to five carbon atoms, e.g., cyclopropyl, and the like.

The term "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

The term "mammal" refers to a human or warm-blooded animals including livestock and companion animals. Livestock refers to animals suitable for human meat consumption. Examples include pigs, cattle, chickens, fish, turkeys, rabbits, etc. Companion animals refer to animals kept as pets such as dogs, cats, etc.

The term "optional" or "optionally" means that the subsequently described event or circumstance may, but need not, occur, and that the description includes instances where the event or circumstance occurs and instances in which it does not.

The term "treating" or "treatment" of a disease includes: (1) preventing the disease, i.e. causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Compounds that have the same molecular formula but differ in the nature or sequence of bonding of their atoms or the arrangement of their atoms in space are termed "isomers". Isomers that differ in the arrangement of their atoms in space are termed "stereoisomers".

It will be appreciated by those skilled in the art that compounds of the invention having a chiral center and may be isolated in optically active and racemic forms. It may also exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

Specifically, a compound of formula I is (5S)-[3-(7-fluoro-1-methyl-2-oxo-2,3-dihydro-1H-indol-5-yl)-2-oxo-oxazolidin-5-ylmethyl]-carbamic acid methyl ester. This compound is substantially free of its opposite enantiomer. The term substantially free means that the desired (5S) enantiomer is at least 95% of the total weight of the racemic mixtures (equivalent to at least 90% enantiomeric excess).

Specifically, a compound of formula I wherein $R^2$ is methyl.

Specifically, a compound of formula I wherein $R^1$ is methyl, ethyl, fluoroethyl, propyl, isopropyl, cyclopropyl, or cyclopropylmethyl.

The compounds of the present invention are generally named according to the IUPAC or CAS nomenclature system. Abbreviations, which are well known to one of ordinary skill in the art, may be used (e.g. "Ph" for phenyl, "Me" for methyl, "Et" for ethyl, "h" for an hour or hours and "rt" for room temperature).

Schemes I and II describe the preparation of compounds of the present invention. The starting materials are prepared by procedures described in these schemes or by procedures known to one of ordinary skill in the art.

Scheme I

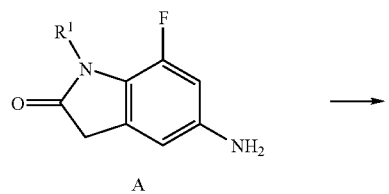

A

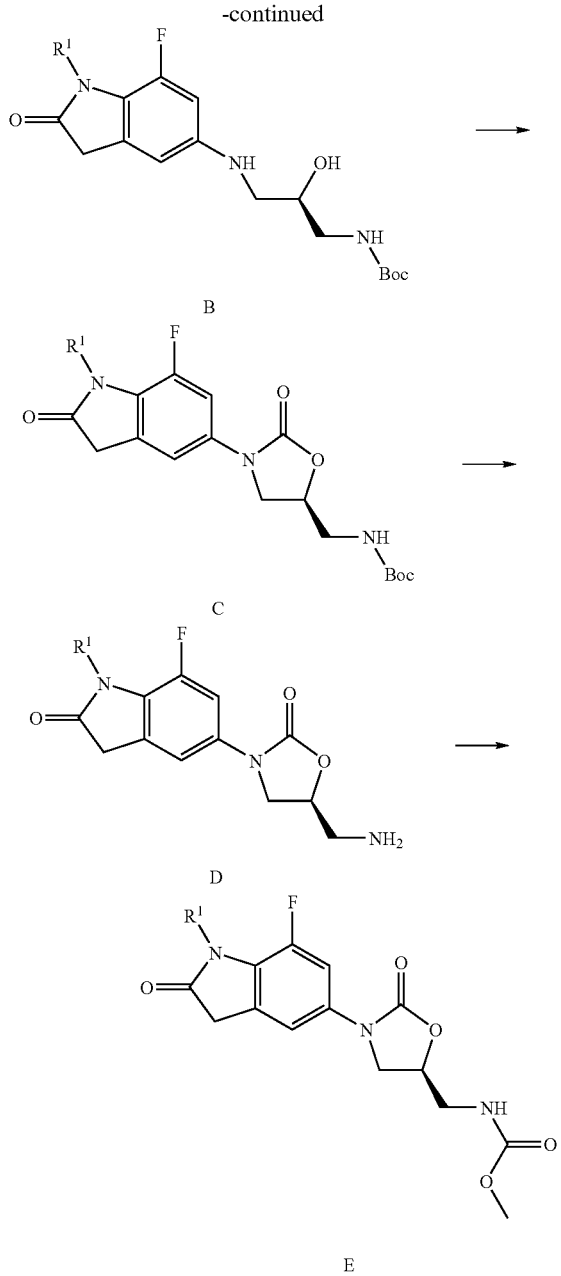

According to Scheme I, the N-substituted-5-amino-7-fluoro-1,3-dihydroindol-2-one (A) is reacted with (S)-oxiranylmethyl-carbamic acid tert-butyl ester in the presence of a Lewis acid such as lithium trifluoromethanesulfonate in a suitable solvent such as acetonitrile at a suitable temperature. (S)-oxiranylmethyl-carbamic acid tert-butyl ester can be conveniently prepared following methods described in WO 02/32857 and WO02/85849. The amino alcohol (B) can then be ring closed using 1,1-carbonylimidazole in solvents such as acetonitrile or tetrahydrofuran at an appropriate temperature or using phosgene in solvent such as methylene chloride or toluene at an appropriate temperature. Boc group in (C) can be deprotected under acid conditions (using acids such as trifluoroacetic acid or hydrochloric acid; Reference: T. W. Greene and P. G. M. Wuts in Protective Groups in Organic Synthesis, 1999, John Wiley & Sons) in a suitable solvent such as methylene chloride or dioxane. The amine in (D) further could be converted to the corresponding methyl carbamate by treating with methyl chloroformate or dimethyl carbonate in the presence of suitable bases such as triethylamine or pyridine to compound (E).

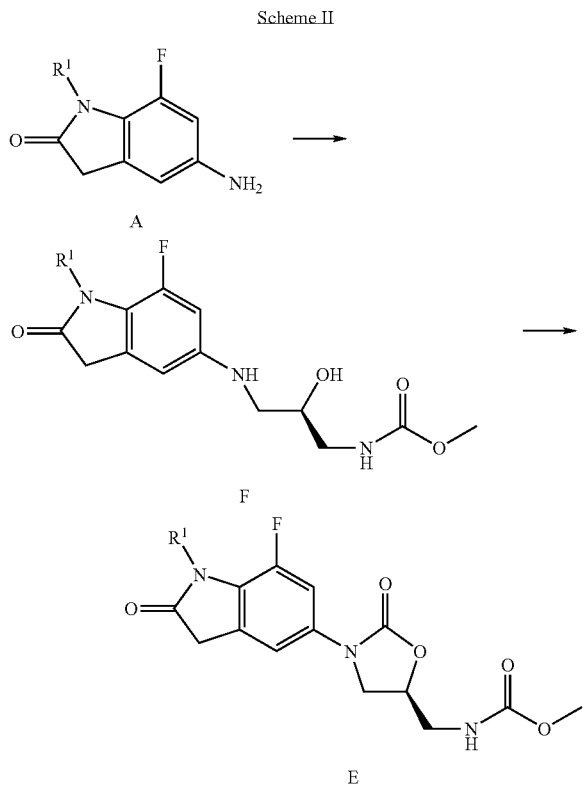

In an alternate Scheme (Scheme II) compound (A) may be reacted with (S)-oxiranylmethyl-carbamic acid methyl ester (WO 99/52855; U.S. Pat. No. 6,417,403) as described in EP 99/00097. The amino alcohol (F) can then be ring closed to give oxazolidinones (E) using 1,1-carbonylimidazole in solvents such as acetonitrile or tetrahydrofuran at an appropriate temperature or using phosgene in solvent such as methylene chloride or toluene at an appropriate temperature.

N-Substituted-5-amino-1,3-dihydroindol-2-one (A) intermediates may be prepared using any of the synthetic procedures described in J. A. Joule, Science of Synthesis, 2001, 10.13, 361-653 pp.

The invention may also provide novel intermediates and novel processes that are useful for preparing compounds of formula I.

Medical and Veterinary Uses

It is known that as a chemical compound class, oxazolidinones generically inhibit monoamine oxidase (MAO), the enzyme responsible for preventing acute blood pressure elevation by the endogenous and dietary amine, tyramine. Accordingly, there is a demand to discover oxazolidinone antibiotics, which possess minimum MAO inhibitory activity to lower risk of potential drug-drug interactions. It has been discovered that, compounds of the present invention have unexceptedly weak MAO inhibitory activity, which indicates it possess the capacity to minimize or eliminate potential drug-drug interactions since strong inhibition of monoamine oxidase can result in altered clearance rates for other compounds normally metabolized by it, including several pharmaceuticals.

The compounds of the present invention may be used for the treatment of infectious, Gram-positive bacterial infections caused by a variety of bacterial organisms, including those that require long-term therapy (>28 days).

Examples of the bacterial organisms include gram-positive bacteria such as multiple resistant staphylococci, for example *S. aureus* and *S. epidermidis*; multiple resistant streptococci, for example *S. pneumoniae* and *S. pyogenes*; and multiple resistant *Enterococci*, for example *E. faecalis*; gram negative aerobic bacteria such as *Haemophilus*, for example *H. influenzae* and *Moraxella*, for example *M. catarrhalis*; as well as anaerobic organisms such as *bacteroides* and *clostridia* species, and acid-fast organisms such as *Mycobacteria*, for example *M. tuberculosis*; and/or *Mycobacterium avium*. Other examples include *Escherichia*, for example *E. coli*. intercellular microbes, for example *Chlamydia* and *Rickettsiae*.

Examples of infections that may be treated with the compounds of the present invention include central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. Specifically, infectious diseases that may be treated with the compounds of the present invention are gram-positive infections such as osteomyelitis, endocarditis and diabetic foot.

Antibacterial and Monoamine Oxidase Inhibition Activities

The in vitro antibacterial activity of the compounds of the present invention may be assessed by following procedures recommended in (1) National Committee for Clinical Laboratory Standards (January 2003), *Methods for dilution antimicrobial tests for bacteria that grow aerobically*, Approved Standard ($6^{th}$ ed), M7-A6, NCCLS, Wayne, Pa.; (2) National Committee for Clinical Laboratory Standards (March 2001), *Methods for antimicrobial susceptibility testing of anaerobic bacteria*, Approved Standard ($5^{th}$ ed), M11-A4, NCCLS, Wayne, Pa.; (3) National Committee for Clinical Laboratory Standards (Jan. 2003), *MIC testing supplemental tables*, M100-S13 (for use with M7-A6), NCCLS, Wayne, Pa.; and (4) Murray P R, Baron E J, Jorgensen J H, et al. *Manual of Clinical Microbiology* ($8^{th}$ ed) Washington, D.C.: American Society for Microbiology Press, 2003. The antibacterial activity can be presented in the form of MIC value. The MIC value is the lowest concentration of drug which prevented macroscopically visible growth under the conditions of the test.

Following procedure may assess monoamine oxidase inhibition activity of the compounds of the present invention:

MAO-A and B inhibition were analyzed by measuring the inhibition of conversion of an MAO substrate, 1-methyl-4-(1-methyl-2-pyrryl)-1,2,3,6-tetrahydropyridine, to its dihydropyridinium metabolite ($\lambda$=421 nm). The substrate concentration was equal to the $K_m$ (64 µM for MAO-A and 43 µM for MAO-B). The MAO-A concentration was 0.01 mg/mL, and the MAO-B concentration was 0.008 mg/mL. Each inhibitor was tested at seven concentrations. Percent inhibition at each concentration was established relative to the uninhibited control rate, and the $IC_{50}$ and $K_i$ values were calculated. A low Ki value indicates that the tested inhibitor possesses a tight binding ability to MAO enzyme, thus, it is a strong MAO inhibitor.

Results of the antibacterial and monoamine oixidase inhibition activities testing for Examples 1 and 2 are shown in Table 1. The antibacterial activities are shown in Table 2.

TABLE 1

| Parameters | Example 1 | Example 2 |
|---|---|---|
| S. aureus (LORSA) $MIC_{90}$ (µg/mL) | 4 | 4 |
| S. pneumoniae (LRSA) $MIC_{90}$(µg/mL) | 4 | 2 |
| E. faecalis (VREF) $MIC_{90}$ (µg/mL) | 4 | 2 |
| E. faecium (VREF) $MIC_{90}$ (µg/mL) | 4 | 2 |
| MAO - A $K_i$ (µM) | 722 | >500 |
| MAO - B $K_i$ (µM) | 52.6 | 3.17 |

TABLE 2

Results of in vitro antibacterial activity $MIC_{90}$ (µg/mL)

| Example No. | S. aureus UC-76 SA-1 | S. pneumoniae SV1 SP-3 | E. faecalis MGH-2 EF 1-1 |
|---|---|---|---|
| 3 | 4 | 4 | 2 |
| 4 | 4 | 4 | 2 |
| 5 | 8 | 4 | 8 |
| 6 | 8 | 8 | 8 |
| 7 | 4 | 4 | 4 |

Pharmaceutical Salts

The compound of formula I may be used in its native form or as a salt. In cases where forming a stable nontoxic acid or base salt is desired, administration of the compound as a pharmaceutically acceptable salt may be appropriate. Examples of pharmaceutically acceptable salts of the present invention include inorganic salts such as hydrochloride, hydrobromide, sulfate, nitrate, bicarbonate, carbonate salts, and organic salts such as tosylate, methanesulfonate, acetate, citrate, malonate, tartarate, succinate, benzoate, ascorbate, etoglutarate, and glycerophosphate.

Pharmaceutically acceptable salts may be obtained using standard procedures well known in the art, for example, reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Routes of Administration

In therapeutic use for treating, or combating, bacterial infections in a mammal (i.e. human and animals), a compound of the present invention or its pharmaceutical compositions can be administered orally, parenterally, topically, rectally, transmucosally, or intestinally.

Parenteral administrations include indirect injections to generate a systemic effect or direct injections to the afflicted area. Examples of parenteral administrations are subcutaneous, intravenous, intramuscular, intradermal, intrathecal, intraocular, intranasal, intravetricular injections or infusions techniques.

Topical administrations include the treatment of infectious areas or organs readily accessibly by local application, such as, eyes, ears including external and middle ear infections, vaginal, open wound, skins including the surface skin and the underneath dermal structures, or other lower intestinal tract. It also includes transdermal delivery to generate a systemic effect.

The rectal administration includes the form of suppositories.

The transmucosal administration includes nasal aerosol or inhalation applications.

The preferred routes of administration are oral and parenteral.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries, which facilitate processing of the active compounds into preparations, which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance, which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mannitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin, as well as soft, sealed capsules made of gelatin and a plasticizer, such as glycerol or sorbitol. The push-fit capsules can contain the active ingredients in a mixture with filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injections, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer. Suitable buffering agents include trisodium orthophosphate, sodium bicarbonate, sodium citrate, N-methylglucamine, L(+)-lysine and L(+)-arginine.

Parenteral administrations also include aqueous solutions of a water-soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use. For suppository administration, the compounds may also be formulated by mixing the agent with a suitable non-irritating excipient, which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or suspensions. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as a benzylalkonium chloride. Alternatively, for ophthalmic uses, the pharmaceutical compositions may be formulated in an ointment such as petrolatum.

In addition to the formulations described previously, the compounds may also be formulated as depot preparations. Such long acting formulations may be in the form of implants. A compound of this invention may be formulated for this route of administration with suitable polymers, hydrophobic materials, or as a sparing soluble derivative such as, without limitation, a sparingly soluble salt.

Additionally, the compounds may be delivered using a sustained-release system. Various sustained-release materials have been established and are well known by those skilled in the art. Sustained-release capsules may, depending on their chemical nature, release the compounds for 24 hours or for up to several days.

Dosage

Pharmaceutical compositions suitable for use in the present invention include compositions wherein the active ingredients are contained in an amount sufficient to achieve the intended purpose, i.e., the treatment or prevent of infectious diseases. More specifically, a therapeutically effective amount means an amount of compound effective to prevent, alleviate or ameliorate symptoms of disease or prolong the survival of the subject being treated.

The quantity of active component, that is the compound of this invention, in the pharmaceutical composition and unit dosage form thereof may be varied or adjusted widely depending upon the manner of administration, the potency of the particular compound and the desired concentration. Determination of a therapeutically effective amount is well within the capability of those skilled in the art. Generally, the quantity of active component will range between 0.5% to 90% by weight of the composition.

Generally, a therapeutically effective amount of dosage of active component will be in the range of about 0.1 to about 400 mg/kg of body weight/day, more preferably about 1.0 to about 50 mg/kg of body weight/day. It is to be understood that the dosages may vary depending upon the requirements of each subject and the severity of the bacterial infection being treated. In average, the effective amount of active component is about 200 mg to 800 mg and preferable 600 mg per day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

In cases of local administration or selective uptake, the effective local concentration of the drug may not be related to plasma concentration and other procedures know in the art may be used to determine the desired dosage amount.

The compounds of this invention can be prepared in accordance with one or more of the methods discussed below. All of the starting materials are either commercially available or can be prepared by procedures that would be well known to one of ordinary skill in organic chemistry. Also, in the discussion the preparations below, the following abbreviations have the following meanings. If an abbreviation is not defined, it has its generally accepted meaning.

| | |
|---|---|
| bm = | broad multiplet |
| BOC = | tert-butoxycarbonyl |
| bd = | broad doublet |
| bs = | broad singlet |
| bt = | broad triplet |
| CDI = | carbodiimidazole |
| d = | doublet |
| dd = | doublet of doublets |
| dq = | doublet of quartets |
| dt = | doublet of triplets |
| dm = | doublet of multiplets |
| DMF = | dimethylformamide |
| DMAP = | dimethylaminopyridine |
| DIEA = | diisopropylethylamine |
| DMSO = | dimethyl sulfoxide |
| eq. = | equivalents |
| g = | grams |
| h = | hours |
| HPLC = | high pressure liquid chromatography |
| HATU = | N-[(dimethylamino)-1H-1,2,3-triazolo-[4,5-b]pyridin-1-yl-methylene]-N-methylmethanaminium hexafluorophosphate N-oxide |
| LG = | leaving group |
| m = | multiplet |
| M = | molar |
| M % = | mole percent |
| max = | maximum |
| meq = | milliequivalent |
| mg = | milligram |
| mL = | milliliter |
| mm = | millimeter |
| mmol = | millimol |
| q = | quartet |
| s = | singlet |
| t or tr = | triplet |
| TBS = | tributylsilyl |
| TFA = | trifluoroacetic acid |
| THF = | tetrahydrofuran |
| TLC = | thin layer chromatography |
| p-TLC = | preparative thin layer chromatography |
| μL = | microliter |
| N = | normality |
| MeOH = | methanol |
| DCM = | dichloromethane |
| HCl = | hydrochloric acid |
| ACN = | acetonitrile |
| MS = | mass spectrometry |
| rt = | room temperature |
| EtOAc = | ethyl acetate |
| EtO = | ethoxy |
| Ac = | acetate |
| NMP = | 1-methyl-2-pyrrolidinone |
| μL = | microliter |
| J = | coupling constant |
| NMR = | Nuclear magnetic resonance |
| MHz = | megahertz |
| Hz = | hertz |
| m/z = | mass to charge ratio |

-continued

| | |
|---|---|
| min = | minutes |
| Boc = | tert-butoxycarbonyl |
| CBZ = | benzyloxycarbonyl |
| DCC = | 1,3-dicyclohexylcarbodiimide |
| PyBop = | benzotriazole-1-yl-oxy-trispyrrolidinophosphonium hexafluorophosphate |

EXAMPLE 1

Preparation of (5S)-[3-(7-fluoro-1-methyl-2-oxo-2,3-dihydro-1H-indol-5-yl)-2-oxo-oxazolidin-5-ylmethyl]-carbamic acid methyl ester

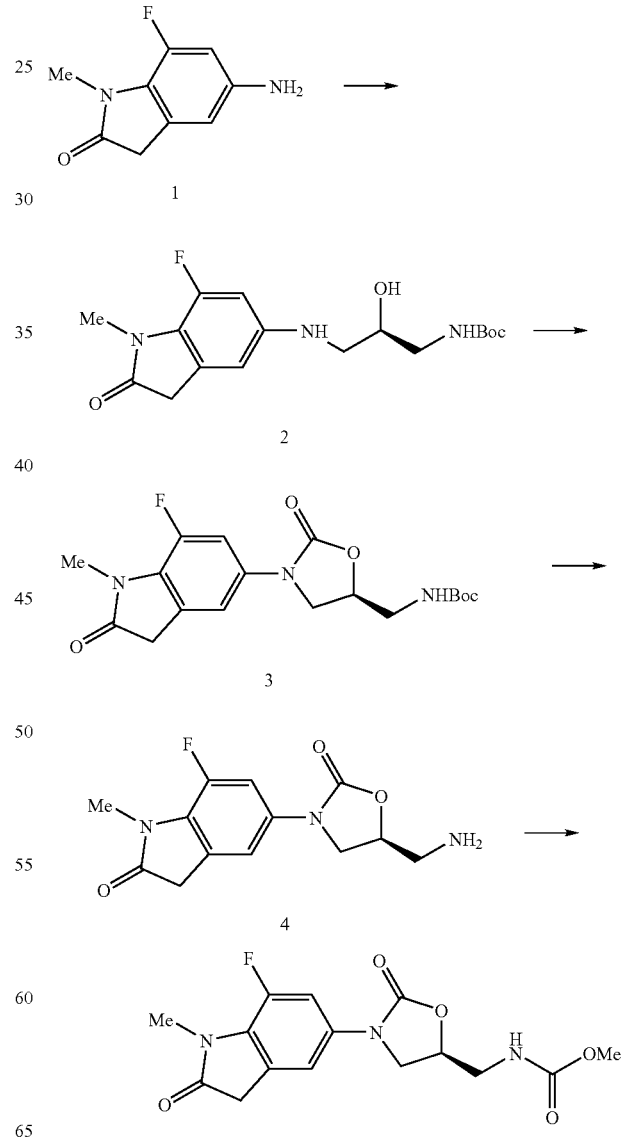

Step 1: Preparation of 7-fluoro-1-methyl-5-nitro-1,3-dihydro-indol-2-one (8)

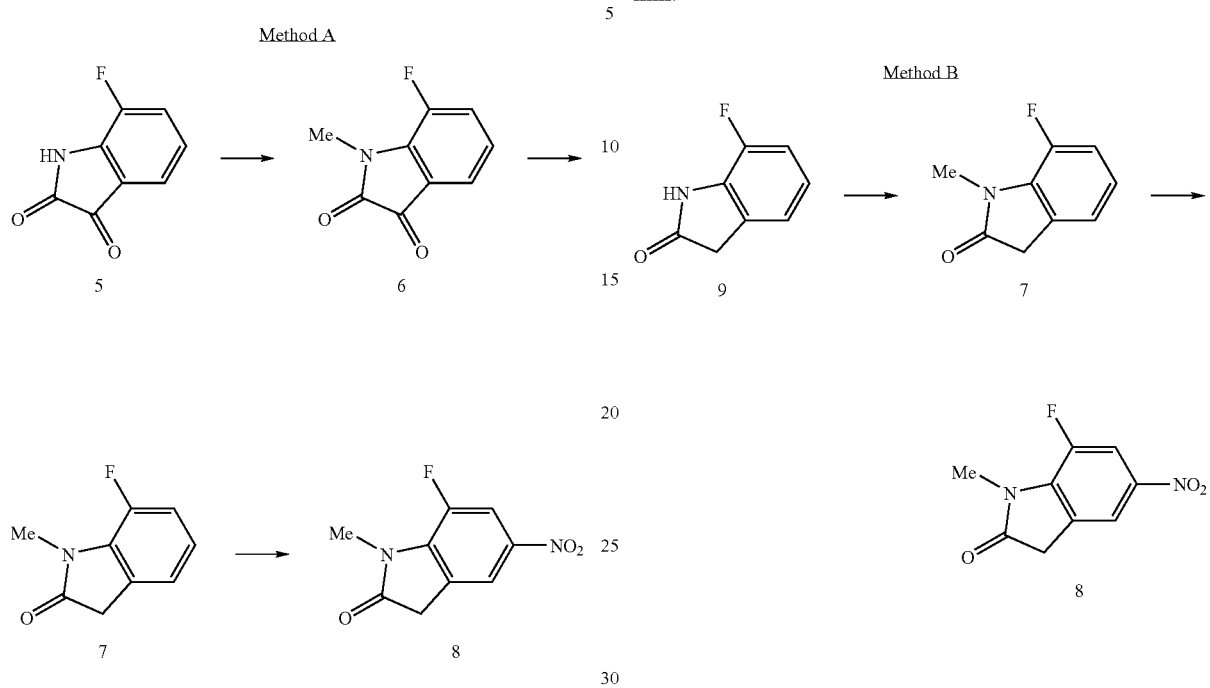

Step 1a: Preparation of 7-fluoro-1-methyl-1H-indole-2,3-dione (6)

7-Fluoro-1H-indole-2,3-dione (5, prepared according to the method of Gassman as described in U.S. Pat. No. 4,188,325, 3.00 g, 0.182 mol), iodomethane (3.40 ml, 0.545 mol) and potassium carbonate (4.92 g, 0.0363 mol) in DMF (15 ml) are stirred at room temperature for 1 hour. The reaction mixture is diluted with cold water and the resulting precipitate filtered and dried to give the title compound as a solid. HPLC r.t. 4.01 min; MS for $C_9H_6FNO_2$ m/z 180.0 $(M+H)^+$.

Step 1b: Preparation of 7-fluoro-1-methyl-1,3-dihydro-indol-2-one (7)

7-Fluoro-1-methyl-1H-indole-2,3-dione (6, 2.48 g, 0.0138 mol) is heated with neat hydrazine hydrate (30 ml) at 130° C. for 30 minutes. The mixture is cooled, diluted with ice water and extracted with ethyl acetate. The extract is washed with brine, dried ($Na_2SO_4$), and evaporated to give the title compound as a solid. HPLC r.t. 4.07 min; MS for $C_9H_8FNO$ m/z 165.16 $(M+H)^+$.

Step 1c: Preparation of 7-fluoro-1-methyl-5-nitro-1,3-dihydro-indol-2-one (8)

7-Fluoro-1-methyl-1,3-dihydro-indol-2-one (7, 2.00 g, 0.0119 mol) is added portion wise to 70% nitric acid (10 ml) at −10° C. After the addition is complete, the reaction is allowed to warm to room temperature and then stirred for 20 hours. The mixture is diluted with ice water and the resulting precipitate filtered, washed with water, and dried under vacuum to give the title compound as a solid. HPLC r.t. 4.40 min.

Step 1a: Preparation of 7-fluoro-1-methyl-1,3-dihydro-indol-2-one (7)

This is similar to the procedure described in G. W. Rewcastle, B. D. Palmer, E. M. Dobrusin, D. W. Fry, A. J. Kracker and W. A. Deny, Journal of Medicinal Chemistry, 1994, 37, 2033-2042. A suspension of the 7-fluoro-1,3-dihydro-indol-2-one (9, 1.0 g, 6.62 mmol.) in $H_2O$ (30 mL) and NaOH (0.397 g, 9.92 mmol., 1.50 eq.) was treated with dimethyl sulfate (1.24 g, 9.86 mmol., 1.49 eq., 0.933 mL; added all at once) and heated to 100° C. for approx. 10 min. and then allowed to cooled to about 50° C. An additional 1.0 eq. of NaOH (0.265 g) and then additional 1 eq. of dimethyl sulfate (0.835 g, 0.626 mL) were added. Again heated to 100° for approx. 10 min. Then cooled to 0° C. in an ice bath and stirred and then filtered off solids, washed several times with water and dried on buchner funnel under vacuum overnight to yield the title compound as a solid. $^1$H NMR (400 MHz, CHLOROFORM-D) δ ppm 3.4 (d, J=2.5 Hz, 3H) 3.5 (s, 2H) 6.9 (m, 3H).

Step 1b: Preparation of 7-fluoro-1-methyl-5-nitro-1,3-dihydro-indol-2-one (8)

To a stirring suspension of trifluoroacetic acid (15 mL) and sodium nitrate (0.381 g, 4.48 mmol) was added 7-fluoro-1-methyl-1,3-dihydro-indol-2-one (7, 0.740 g, 4.48 mmol) and the reaction stirred at room temp. After 3½ hrs material poured onto ice water, filtered off resulting a precipitate. Dried on buchner funnel under vacuum overnight to give the title compound. $^1$H NMR (400 MHz, CHLOROFORM-D) δ ppm 3.4 (d, J=2.7 Hz, 3H) 3.6 (s, 2H) 8.0 (m, 2H).

Method C

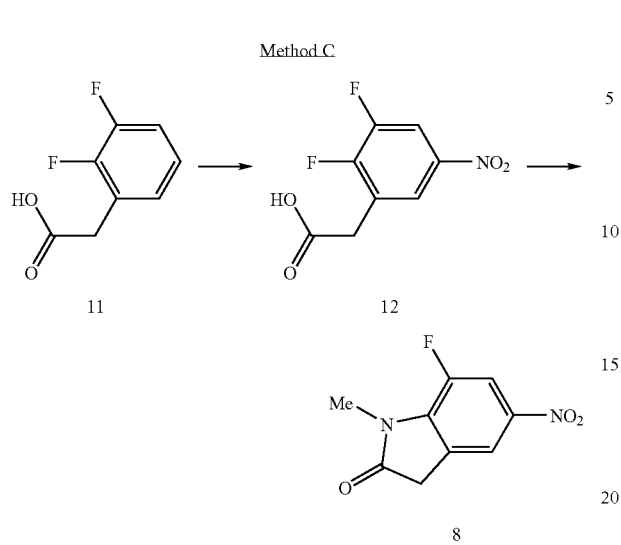

Step 1a: Preparation of (2,3-difluoro-5-nitrophenyl)acetic acid (12)

(2,3-Difluoro-phenyl)-acetic acid (11, 5 g, 0.0290 mol) is dissolved in concentrated sulfuric acid (20 ml) and the resulting solution cooled to −10° C. with vigorous stirring. A solution of nitric acid (1.88 ml, 69.3%, 0.0290 mol) and sulfuric acid (2 ml) is added dropwise at a rate such that the temperature remains below −5° C. The thickened slurry is stirred for 15 minutes and then poured on ice. The resulting white precipitate is filtered and dried under vacuum (6.3 g, 99%) and consists of a 50/50 mixture of 5 and 6-$NO_2$ regioisomers suitable for use directly in the next step.

Step 1b: Preparation of 7-fluoro-1-methyl-5-nitro-1,3-dihydro-indol-2-one (8)

Crude (2,3-difluoro-5-nitrophenyl)acetic acid (12, 1.00 g, 0.00461 mol) and a 40% solution of methylamine in water (3 eq., 1.20 ml, 0.0138 mol) are mixed in DMSO (5 ml) and stirred at 45° C. for 1 hour. 2N Hydrochloric acid (20 ml) is added in one portion and the mixture stirred at room temperature for 1 hour. The reaction mixture is extracted with ethyl acetate and the extract washed with saturated aqueous sodium bicarbonate and brine, dried ($MgSO_4$) and evaporated. The residue is purified by flash column chromatography (50% ethyl acetate/hexane) to give the title compound as a solid. HPLC r.t. 4.4 min.

Method D

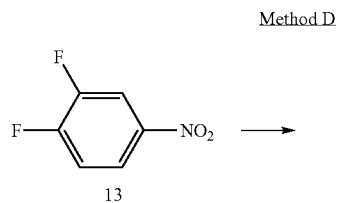

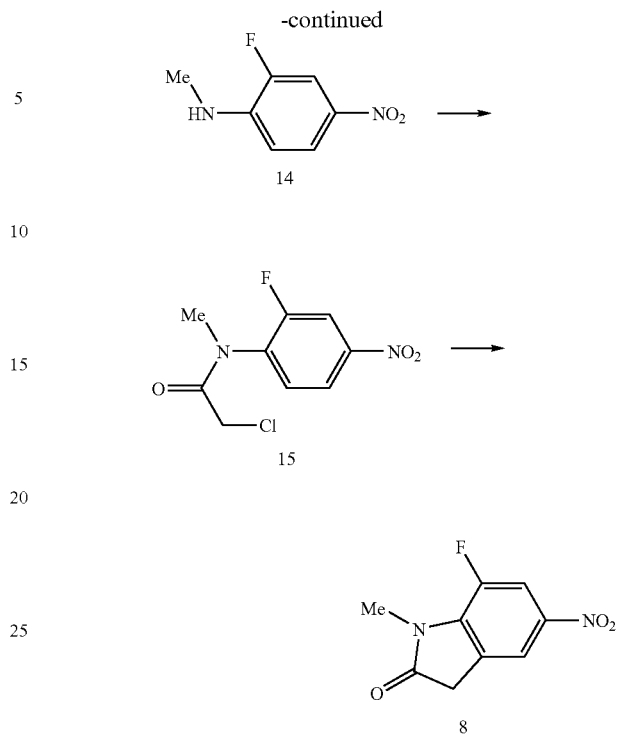

Step 1a: Preparation of (2-fluoro-4-nitro-phenyl)-methyl-amine (14)

To 3,4-difluoro-nitrobenzene (13, 5.0 g, 31.4 mmol) taken in dimethyl sulfoxie (30 mL) was added 40% aqueous methylamine in portions. The reaction was stirred at room temperature for 30 minutes. The reaction was diluted with 150 mL of water and the resulting precipitate was filtered and dried under vacuum to obtain solid (5.34 g) in 98% isolated yield.

Step 1b: Preparation of 2-chloro-N-(2-fluoro-4-nitro-phenyl)-N-methyl-acetamide (15)

Chloroacetyl chloride (1.87 ml, 0.0235 mol) is added to (2-fluoro-4-nitro-phenyl)-methyl-amine (14, 2.00 g, 0.0118 mol) in toluene (20 ml) and the mixture refluxed for 3 hours. The mixture is evaporated under vacuum and the residue triturated with ethanol to give the title compound as a white solid. HPLC r.t. 4.57 min; MS for $C_9H_8ClFN_2O_3$ m/z 247 $(M+H)^+$.

Step 1c: Preparation of 7-fluoro-1-methyl-5-nitro-1,3-dihydro-indol-2-one (8)

Following the method described by Hennessy and Buchwald in J. Am. Chem. Soc., 2003, 125, 12084-12085, 2-chloro-N-(2-fluoro-4-nitro-phenyl)-N-methyl-acetamide (15, 1.00 g, 4.05 mol), palladium acetate (27.3 mg, 0.122 mmol) and 2-(di-tert-butylphosphino)biphenyl (72.5 mg, 0.243 mmol) are placed under a nitrogen atmosphere, and toluene (20 ml) and triethylamine (0.85 ml, 6.08 mmol) are added via syringe. The reaction is heated at 80° C. for 4 hours and then evaporated to dryness. The dark residue is purified by PTLC (dichloromethane) to give the title compound as a light brownish-orange solid. HPLC r.t. 4.4 min.

Step 2: Preparation of 5-Amino-7-fluoro-1-methyl-1,3-dihydro-indol-2-one (1)

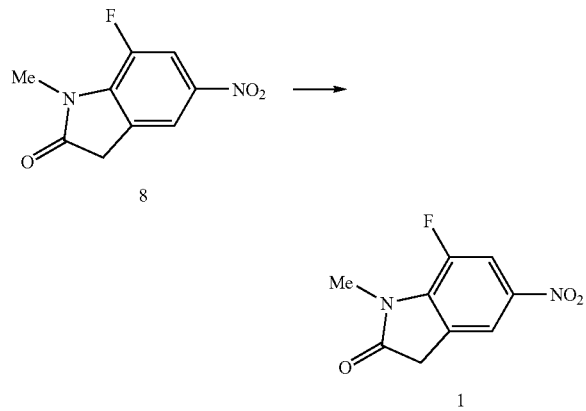

Method A

Iron powder (2.27 g, 0.0405 mol) is added in small portions to 7-fluoro-1-methyl-5-nitro-1,3-dihydro-indol-2-one (Step 1c, 2.13 g, 0.0101 mol) and ammonium chloride (5.30 g, 0.101 mol) in ethanol (100 ml) and water (50 ml) at 90° C. The reaction mixture is stirred vigorously and heated for 30 min, cooled to room temperature, and diluted with dichloromethane (100 ml). The mixture is filtered through celite, the organic layer separated and washed with water and brine, dried over sodium sulfate and evaporated to give the title compound as a solid. HPLC r.t. 2.17 min; MS for $C_9H_9FN_2O$ m/z 181.0 $(M+H)^+$.

Method B

To 7-fluoro-1-methyl-5-nitro-1,3-dihydro-indol-2-one (8, 1 g, 4.76 mmol) taken in tetrahydrofuran (50 mL) in a Parr shaker and was added Raney nickel (g) and the reaction vessel was pressurized with hydrogen at 50 psi. The reaction mixture was shaken at 50° C. for 12 hours. The catalyst was filtered off and the solvents were evaporated to obtain the title compound as a solid. $^1$H NMR (400 MHz, DMSO-d6) δ ppm 3.1 (s, 3H), 3.4 (s, 2H), 5.0 (s, 2H), 6.2 (dd, J=13.9, 2.0 Hz, 1H), 6.3 (s, 1H).

Step 3: Preparation of (5R)-[3-(7-fluoro-1-methyl-2-oxo-2,3-dihydro-1H-indol-5-ylamino)-2-hydroxy-propyl]-carbamic acid tert-butyl ester (2)

5-Amino-7-fluoro-1-methyl-1,3-dihydro-indol-2-one (1, 1.72 g, 9.54 mmol), (S)-oxiranylmethyl-carbamic acid tert-butyl ester (1.66 g, 9.54 mmol) and lithium trifluoromethanesulfonate (1.46 g, 9.54 mmol) in acetonitrile (15 ml) are heated at 90° C. for 2 hours. The reaction mixture is diluted with ethyl acetate, washed with water and brine, dried $(Na_2SO_4)$ and evaporated. Final purification by flash chromatography (70% Ethyl acetate/hexane) gives the title compound as a solid. HPLC R.T. 3.75 min; MS for $C_{17}H_{24}FN_3O_4$ m/z 354 $(M+H)^+$.

Step 4: Preparation of (5S)-[3-(7-fluoro-1-methyl-2-oxo-2,3-dihydro-1H-indol-5-yl)-2-oxo-oxazolidin-5-ylmethyl]-carbamic acid tert-butyl ester (3)

Phosgene (20% solution in toluene, 2.70 ml, 0.0276 mol) is added to (5R)-[3-(7-fluoro-1-methyl-2-oxo-2,3-dihydro-1H-indol-5-ylamino)-2-hydroxy-propyl]-carbamic acid tert-butyl ester (2, 1.30 g, 0.00368 mol) and triethylamine (2.55 ml, 0.0184 mol) in dichloromethane (15 ml) at 0° C. and stirred for 30 minutes. The mixture is diluted with dichloromethane, washed with water and brine, dried $(Na_2SO_4)$ and evaporated. The residue is purified by flash column chromatography (65 to 75% Ethyl acetate/hexane) to give the title compound as a solid. HPLC r.t. 4.68 min; MS for $C_{18}H_{22}FN_3O_5$ m/z 380 $(M+H)^+$.

Step 5: Preparation of 5-(5R-aminomethyl-2-oxo-oxazolidin-3-yl)-7-fluoro-1-methyl-1,3-dihydro-indol-2-one (4)

(5S)-[3-(7-Fluoro-1-methyl-2-oxo-2,3-dihydro-1H-indol-5-yl)-2-oxo-oxazolidin-5-ylmethyl]-carbamic acid tert-butyl ester (3, 0.320 g, 0.843 mmol) is treated with 50% TFA/DCM (4 ml) for 15 minutes at room temperature. The reaction is evaporated and the product isolated as the TFA salt. HPLC r.t. 2.84 min; MS for $C_{13}H_{14}FN_3O_3$ m/z 280 $(M+H)^+$.

Step 6: Preparation of (5S)-[3-(7-fluoro-1-methyl-2-oxo-2,3-dihydro-1H-indol-5-yl)-2-oxo-oxazolidin-5-ylmethyl]-carbamic acid methyl ester Methyl chloroformate (0.099 ml, 1.25 mmol) is added dropwise to 5-(5R-aminomethyl-2-oxo-oxazolidin-3-yl)-7-fluoro-1-methyl-1,3-dihydro-indol-2-one (4, 0.330 g, 0.838 mmol) and diisopropylethylamine (0.612 ml, 3.35 mmol) in dichloromethane (5 ml) at 0° C. The reaction is stirred at 0° C. for 30 minutes and then allowed to warm at room temperature. The reaction mixture is diluted with dichloromethane, washed with water, citric acid and brine, dried $(Na_2SO_4)$ and evaporated. The residue is purified to give the title compound as a solid. HPLC r.t. 3.75 min; $^1$H NMR (300 MHz, CDCl$_3$) δ7.30 (d, J=1.2 Hz, 1H), 7.22 (dd, J=2.1, 14 Hz, 1H), 5.14 (br s, 1H), 4.73-4.81 (m, 1H), 4.02 (t, J=9 Hz, 1H), 3.80 (dd, J=6.6, 9 Hz, 1H), 3.69 (s, 3H), 3.55 (s, 2H), 3.50-3.65 (m, 2H), 3.40 (d, J=2.4 Hz, 3H); MS for $C_{15}H_{16}FN_3O_5$ m/z 338 $(M+H)^+$.

EXAMPLE 2

Preparation of (5S)-[3-(7-fluoro-1-isopropyl-2-oxo-2,3-dihydro-1H-indol-5-yl)-2-oxo-oxazolidin-5-ylmethyl]-carbamic acid methyl ester

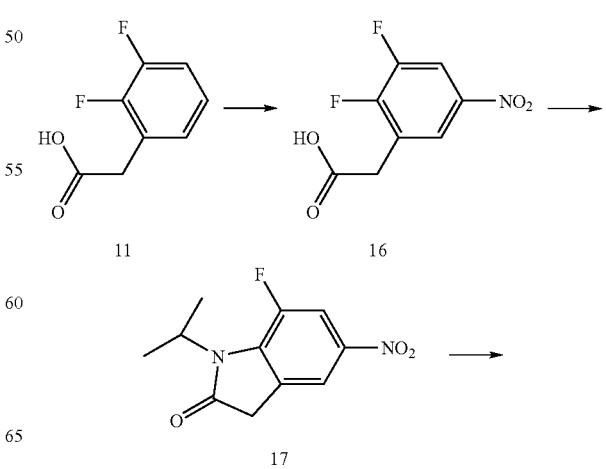

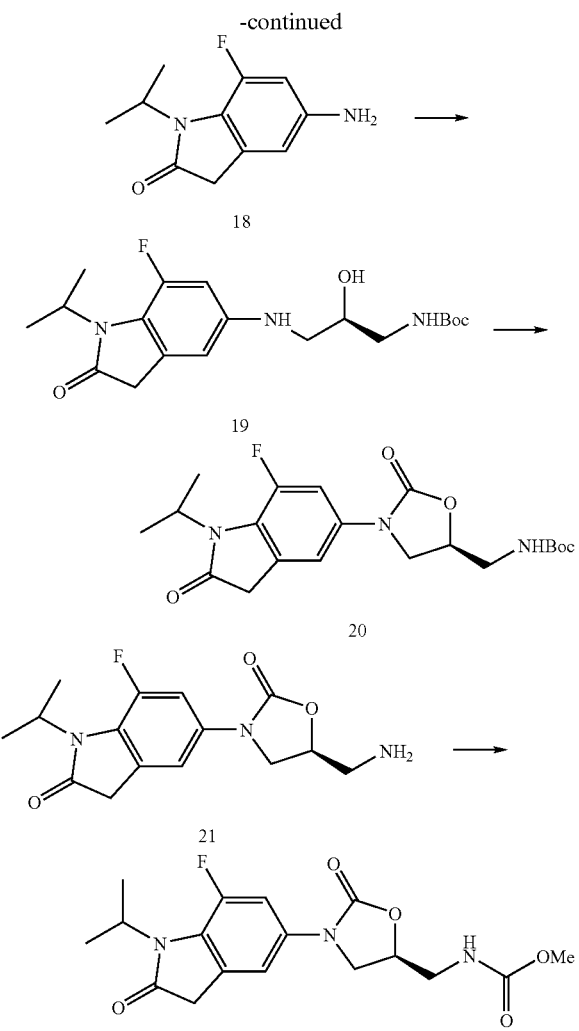

Step 1: Preparation of (2,3-difluoro-5-nitrophenyl) acetic acid (16)

2,3-Difluoro-phenyl)-acetic acid (11, 5 g, 0.0290 mol) is dissolved in concentrated sulfuric acid (20 ml) and the resulting solution cooled to −10° C. with vigorous stirring. A solution of nitric acid (1.88 ml, 69.3%, 0.0290 mol) and sulfuric acid (2 ml) is added dropwise at a rate such that the temperature remains below −5° C. The thickened slurry is stirred for 15 minutes and then poured on ice. The resulting precipitate is filtered and dried under vacuum (6.3 g, 99%) and consists of a 50/50 mixture of 5 and 6-$NO_2$ regioisomers suitable for use directly in the next step.

Step 2: Preparation of 7-fluoro-1-isopropyl-5-nitro-1,3-dihydro-indol-2-one (17)

Crude (2,3-difluoro-5-nitrophenyl)acetic acid (16, 1.00 g, 0.00461 mol) and isopropylamine (6 eq., 2.35 ml, 0.0276 mol) are mixed in DMSO (5 ml) and stirred at 45° C. for 1 hour. 2N Hydrochloric acid (20 ml) is added in one portion and the mixture stirred at room temperature for 1 hour. The resulting precipitate is filtered, washed with water and ether, and dried under vacuum (0.39 g, 35%); HPLC r.t. 5.31 min.

Step 3: Preparation of 5-amino-7-fluoro-1-isopropyl-1,3-dihydro-indol-2-one (18)

Iron powder (0.854 g, 15.3 mmol) is added portionwise to a mixture of 7-fluoro-1-isopropyl-5-nitro-1,3-dihydro-indol-2-one (17, 0.91 g, 3.82 mmol) and ammonium chloride (2.04 g, 38.2 mmol) in ethanol (50 ml) and water (25 ml) at 90° C. The reaction is stirred vigorously and heated for 30 min, cooled to room temperature and diluted with dichloromethane (150 mL). The mixture is filtered through celite, the organic layer separated and washed with water and brine, dried over sodium sulfate and evaporated to give the title compound as a solid. HPLC r.t. 2.97 min; MS for $C_{11}H_{13}FN_2O$ m/z 209.1 $(M+H)^+$.

Step 4: Preparation of (5R)-[3-(7-fluoro-1-isopropyl-2-oxo-2,3-dihydro-1H-indol-5-ylamino)-2-hydroxy-propyl]-carbamic acid tert-butyl ester (19)

5-Amino-7-fluoro-1-isopropyl-1,3-dihydro-indol-2-one (18, 2.33 g, 11.2 mmol), (S)-oxiranylmethyl-carbamic acid tert-butyl ester (1.94 g, 11.2 mmol) and lithium trifluoromethanesulfonate (1.73 g, 11.2 mmol) in acetonitrile (20 ml) are heated at 70° C. for 2 hours. The reaction mixture is diluted with ethyl acetate, washed with water and brine, dried ($Na_2SO_4$) and evaporated. Final purification by flash chromatography (70% ethyl acetate/hexane) gives the title compound as a solid. HPLC r.t. 4.32 min; MS for $C_{19}H_{28}FN_3O_4$ m/z 382.3 $(M+H)^+$.

Step 5: Preparation of (5S)-[3-(7-fluoro-1-isopropyl-2-oxo-2,3-dihydro-1H-indol-5-yl)-2-oxo-oxazolidin-5-ylmethyl]-carbamic acid tert-butyl ester (20)

Phosgene (20% solution in toluene, 3.53 ml, 36.2 mmol) is added to (5R)-[3-(7-fluoro-1-isopropyl-2-oxo-2,3-dihydro-1H-indol-5-ylamino)-2-hydroxy-propyl]-carbamic acid tert-butyl ester (19, 1.84 g, 4.82 mmol) and triethylamine (3.33 ml, 24.1 mmol) in dichloromethane (20 ml) at 0° C. The reaction is allowed to warm to room temperature and stirred for 1 hour. The mixture is diluted with dichloromethane, washed with water and brine, dried ($Na_2SO_4$) and evaporated to give the title compound suitable for use directly in the next step. HPLC r.t. 5.28 min; MS for $C_{20}H_{26}FN_3O_5$ m/z 408 $(M+H)^+$.

Step 6: Preparation of 5-(5R-aminomethyl-2-oxo-oxazolidin-3-yl)-7-fluoro-1-isopropyl-1,3-dihydro-indol-2-one (21)

(5S)-[3-(7-Fluoro-1-isopropyl-2-oxo-2,3-dihydro-1H-indol-5-yl)-2-oxo-oxazolidin-5-ylmethyl]-carbamic acid tert-butyl ester (20, 0.345 g, 0.665 mmol) is treated with 50% TFA/DCM (4 ml) for 30 minutes at room temperature. The reaction is evaporated and the product isolated as the TFA salt. HPLC r.t. 3.43 min; MS for $C_{15}H_{18}FN_3O_3$ m/z 308 $(M+H)^+$.

Step 7: Preparation of (5S)-[3-(7-fluoro-1-isopropyl-2-oxo-2,3-dihydro-1H-indol-5-yl)-2-oxo-oxazolidin-5-ylmethyl]-carbamic acid methyl ester (Example 2)

Methyl chloroformate (0.097 ml, 1.26 mmol) is added dropwise to 5-(5-aminomethyl-2-oxo-oxazolidin-3-yl)-7-fluoro-1-isopropyl-1,3-dihydro-indol-2-one (21, 0.355 g, 0.842 mmol) and diisopropylethylamine (0.616 ml, 3.37 mmol) in dichloromethane (4 ml) at 0° C. The reaction is stirred at 0° C. for 30 minutes and then allowed to warm at room temperature. The reaction mixture is diluted with dichloromethane, washed with water, citric acid and brine, dried ($Na_2SO_4$) and evaporated. The residue is purified to give the title compound as a solid. HPLC r.t. 4.42 min; $^1$H NMR (300 MHz, $CDCl_3$) δ7.33 (d, J=1.2 Hz, 1H), 7.24 (dd, J=2.1, 14 Hz, 1H), 5.14 (br s, 1H), 4.80-4.92 (m, 1H), 4.75-4.84 (m, 1H), 4.05 (t, J=8.7 Hz, 1H), 3.81 (dd, J=6.6, 9 Hz, 1H), 3.71 (s, 3H), 3.57 (s, 2H), 3.52-3.65 (m, 2H), 1.44 (d, J=6.9 Hz, 6H); MS for $C_{17}H_{20}FN_3O_5$ m/z 366 (M+H)$^+$.

EXAMPLE 3

Preparation of (S)-[3-(1-ethyl-7-fluoro-2-oxo-2,3-dihydro-1H-indol-5-yl)-2-oxo-oxazolidin-5-ylmethyl]-carbamic acid methyl ester

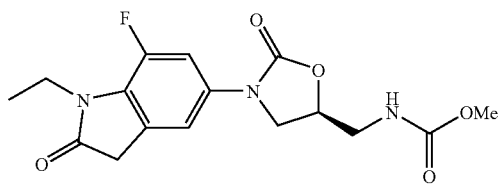

Step 1: Preparation of 1-ethyl-7-fluoro-1H-indole-2,3-dione

7-Fluoro-1H-indole-2,3-dione (prepared according to the method of Gassman as described in U.S. Pat. No. 4,188,325 (4.00 g, 24.2 mmol), iodoethane (3.87 ml, 48.5 mmol) and potassium carbonate (6.61 g, 48.5 mmol) in DMF (20 ml) are stirred at room temperature for 20 hours. The reaction mixture is diluted with cold water and the resulting precipitate filtered and dried to give the title compound as an orange solid. HPLC r.t. 4.48 min; MS for $C_{10}H_8FNO_2$ m/z 193.9 (M+H)$^+$.

Step 2: Preparation of 1-ethyl-7-fluoro-1,3-dihydro-indol-2-one

1-Ethyl-7-fluoro-1H-indole-2,3-dione (3.60 g, 18.6 mmol) is heated with neat hydrazine hydrate (15 ml) at 130° C. for 60 minutes. The mixture is cooled, diluted with ice water and extracted with ethyl acetate. The extract is washed with brine, dried ($Na_2SO_4$), and evaporated to give the title compound as an orange solid. HPLC r.t. 4.60 min; MS for $C_{10}H_{10}FNO$ m/z 198.1 (M+H)$^+$.

Step 3: Preparation of 1-ethyl-7-fluoro-5-nitro-1,3-dihydro-indol-2-one

1-Ethyl-7-fluoro-1,3-dihydro-indol-2-one (3.45 g, 19.3 mmol) is added portionwise to a mixture of sodium nitrate (1.64 g, 19.3 mmol) and trifluoroacetic acid (60 ml) and stirred at room temperature for 5 hours. The reaction is diluted with ice water and the resulting precipitate filtered, washed with water, and dried under vacuum to give the title compound as a brownish-yellow solid. HPLC r.t. 4.88 min; MS for $C_{10}H_9FN_2O_3$ m/z 223.0 (M-H)$^-$.

Step 4: Preparation of 5-amino-1-ethyl-7-fluoro-1,3-dihydro-indol-2-one

Iron powder (3.84 g, 68.7 mmol) is added in small portions to 1-ethyl-7-fluoro-5-nitro-1,3-dihydro-indol-2-one (3.85 g, 17.2 mmol) and ammonium chloride (8.94 g, 171 mmol) in ethanol (150 ml) and water (75 ml) at 90° C. The reaction mixture is stirred vigorously and heated for 30 min, cooled to room temperature, and diluted with dichloromethane (600 ml). The mixture is filtered through celite, the organic layer separated and washed with water and brine, dried over sodium sulfate and evaporated to give the title compound as a yellow solid. HPLC r.t. 2.60 min; MS for $C_{10}H_{11}FN_2O$ m/z 195.0 (M+H)$^+$.

Step 5: Preparation of (R)-[3-(1-ethyl-7-fluoro-2-oxo-2,3-dihydro-1H-indol-5-ylamino)-2-hydroxy-propyl]-carbamic acid tert-butyl ester 5-Amino-1-ethyl-7-fluoro-1,3-dihydro-indol-2-one (2.25 g, 11.6 mmol), (S)-oxiranylmethyl-carbamic acid tert-butyl ester (2.00 g, 11.6 mmol) and lithium trifluoromethanesulfonate (1.80 g, 11.6 mmol) in acetonitrile (12 ml) are heated at 90° C. for 20 hours. The reaction mixture is diluted with ethyl acetate, washed with water and brine, dried ($Na_2SO_4$) and evaporated. Final purification by flash chromatography (70% Ethyl acetate/hexane) gives the title compound as a yellow-brown foamy solid. HPLC r.t. 3.95 min; MS for $C_{18}H_{26}FN_3O_4$ m/z 368.3 (M+H)$^+$.

Step 6: Preparation of (S)-[3-(1-ethyl-7-fluoro-2-oxo-2,3-dihydro-1H-indol-5-yl)-2-oxo-oxazolidin-5-ylmethyl]-carbamic acid tert-butyl ester Phosgene (20% solution in toluene, 3.58 ml, 36.7 mmol) is added to (R)-[3-(1-ethyl-7-fluoro-2-oxo-2,3-dihydro-1H-indol-5-ylamino)-2-hydroxy-propyl]-carbamic acid tert-butyl ester (1.80 g, 4.89 mmol) and triethylamine (3.38 ml, 24.5 mmol) in dichloromethane (20 ml) at 0° C. and stirred for 30 minutes. The mixture is diluted with dichloromethane, washed with water and brine, dried ($Na_2SO_4$) and evaporated to give the title compound as a light brown solid. HPLC r.t. 4.92 min; MS for $C_{19}H_{24}FN_3O_5$ m/z 394.1 (M+H)$^+$.

Step 7: Preparation of (R)-5-(5-aminomethyl-2-oxo-oxazolidin-3-yl)-1-ethyl-7-fluoro-1,3-dihydro-indol-2-one (S)-[3-(1-Ethyl-7-fluoro-2-oxo-2,3-dihydro-1H-indol-5-yl)-2-oxo-oxazolidin-5-ylmethyl]-carbamic acid tert-butyl ester (0.325 g, 0.826 mmol) is treated with 50% TFA/DCM (4 ml) for 15 minutes at room temperature. The reaction is evaporated and the title compound isolated as the TFA salt. HPLC r.t. 3.13 min; MS for $C_{14}H_{16}FN_3O_3$ m/z 294.0 (M+H)$^+$.

Step 8: Preparation of (S)-[3-(1-ethyl-7-fluoro-2-oxo-2,3-dihydro-1H-indol-5-yl)-2-oxo-oxazolidin-5-ylmethyl]-carbamic acid methyl ester Methyl chloroformate (0.117 ml, 1.53 mmol) is added dropwise to (R)-5-(5-aminomethyl-2-oxo-oxazolidin-3-yl)-1-ethyl-7-fluoro-1,3-dihydro-indol-2-one (0.414 g, 1.02 mmol) and diisopropylethylamine (0.709 ml, 4.06 mmol) in dichloromethane (5 ml) at 0° C. The reaction is stirred at 0° C. for 30 minutes and then allowed to warm at room temperature. The reaction mixture is diluted with dichloromethane, washed with water and brine, dried (Na$_2$SO$_4$) and evaporated. The residue is purified by PTLC (5% MeOH/DCM) to give the title compound as a yellow solid. HPLC r.t. 4.04 min; $^1$H NMR (300 MHz, CDCl$_3$) 7.30 (s, 1H), 7.23 (dd, J=2, 13.2 Hz, 1H), 5.13 (t, 1H), 4.74-4.81 (m, 1H), 4.03 (t, J=9.2 Hz, 1H), 3.90 (q, J=6.8 Hz, 2H), 3.80 (dd, J=6.8, 9.2 Hz, 1H), 3.69 (s, 3H), 3.53-3.67 (m, 2H), 1.28 (t, J=6.8 Hz, 3H); MS for C$_{16}$H$_{18}$FN$_3$O$_5$ m/z 352.1 (M+H)$^+$.

EXAMPLE 4

Preparation of (S)-{3-[7-fluoro-1-(2-fluoro-ethyl)-2-oxo-2,3-dihydro-1H-indol-5-yl]-2-oxo-oxazolidin-5-ylmethyl}-carbamic acid methyl ester

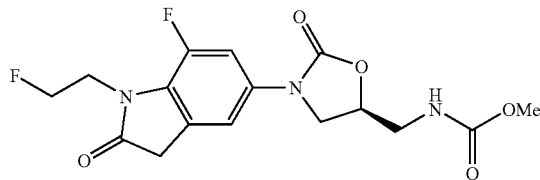

Step 1: Preparation of 7-fluoro-1-(2-fluoro-ethyl)-1H-indole-2,3-dione

7-Fluoro-1H-indole-2,3-dione (prepared according to the method of Gassman as described in U.S. Pat. No. 4,188,325 (2.00 g, 12.1 mmol), 1-iodo-2-fluoroethane (4.21 g, 24.2 mmol) and potassium carbonate (3.30 g, 24.2 mmol) in DMF (20 ml) are stirred at room temperature for 20 hours. The reaction mixture is diluted with cold water and the resulting precipitate filtered and dried to give the title compound as an orange solid. HPLC r.t. 4.18 min; MS for C10H7F2NO2 m/z 212.1 (M+H)$^+$.

Step 2: Preparation of 7-fluoro-1-(2-fluoro-ethyl)-1, 3-dihydro-indol-2-one

7-Fluoro-1-(2-fluoro-ethyl)-1H-indole-2,3-dione (1.04 g, 4.92 mmol) is heated with neat hydrazine hydrate (10 ml) at 130° C. for 20 minutes. The mixture is cooled, diluted with ice water and extracted with ethyl acetate. The extract is washed with brine, dried (Na$_2$SO$_4$), and evaporated to give the title compound as a brown solid. HPLC r.t. 4.36 min; MS for C10H9F2NO m/z 198.1 (M+H)$^+$.

Step 3: Preparation of 7-fluoro-1-(2-fluoro-ethyl)-5-nitro-1,3-dihydro-indol-2-one 7-Fluoro-1-(2-fluoro-ethyl)-1,3-dihydro-indol-2-one (0.880 g, 0.0119 mol) is added portionwise to 70% nitric acid (8 ml) at −10° C. After the addition is complete, the reaction is allowed to warm to room temperature and then stirred for 24 hours. The mixture is diluted with ice water and the resulting precipitate filtered, washed with water, and dried under vacuum to give the title compound as a light brown solid. HPLC r.t. 4.65 min; MS for C10H8F2N2O3 m/z 243.3 (M+H)$^+$.

Step 4: Preparation of 5-amino-7-fluoro-1-(2-fluoro-ethyl)-1,3-dihydro-indol-2-one Iron powder (0.416 g, 7.43 mmol) is added in small portions to 7-fluoro-1-(2-fluoro-ethyl)-5-nitro-1,3-dihydro-indol-2-one (Step 3, 0.45 g, 1.86 mmol) and ammonium chloride (0.987 g, 18.6 mmol) in ethanol (40 ml) and water (20 ml) at 90° C. The reaction mixture is stirred vigorously and heated for 30 min, cooled to room temperature, and diluted with dichloromethane (100 ml). The mixture is filtered through celite, the organic layer separated and washed with water and brine, dried over sodium sulfate and evaporated to give the title compound as a dark brown solid. HPLC r.t. 2.34 min; MS for C10H10F2N2O m/z 213.2 (M+H)$^+$.

Step 5: Preparation of (R)-{3-[7-fluoro-1-(2-fluoro-ethyl)-2-oxo-2,3-dihydro-1H-indol-5-ylamino]-2-hydroxy-propyl}-carbamic acid tert-butyl ester 5-Amino-7-fluoro-1-(2-fluoro-ethyl)-1,3-dihydro-indol-2-one (0.39 g, 1.84 mmol), (S)-oxiranylmethyl-carbamic acid tert-butyl ester (0.319 g, 1.84 mmol) and lithium trifluoromethanesulfonate (0.283 g, 1.84 mmol) in acetonitrile (4 ml) are heated at 90° C. for 6 hours. The reaction mixture is diluted with ethyl acetate, washed with water and brine, dried (Na$_2$SO$_4$) and evaporated. Final purification by flash chromatography (70% Ethyl acetate/hexane) gives the title compound as a yellow-brown foamy solid. HPLC r.t. 3.92 min; MS for C18H25F2N3O4 m/z 386.1 (M+H)$^+$.

Step 6: Preparation of (S)-{3-[7-fluoro-1-(2-fluoro-ethyl)-2-oxo-2,3-dihydro-1H-indol-5-yl]-2-oxo-oxazolidin-5-ylmethyl}-carbamic acid tert-butyl ester Phosgene (20% solution in toluene, 0.414 ml, 4.24 mmol) is added to (R)-{3-[7-fluoro-1-(2-fluoro-ethyl)-2-oxo-2,3-dihydro-1H-indol-5-ylamino]-2-hydroxy-propyl}-carbamic acid tert-butyl ester (0.150 g, 0.424 mmol) and triethylamine (0.295 ml, 2.12 mmol) in dichloromethane (3 ml) at 0° C. and stirred for 30 minutes. The mixture is diluted with dichloromethane, washed with water and brine, dried (Na$_2$SO$_4$) and evaporated to give the title compound as a light brown solid. HPLC r.t. 4.70 min; MS for C19H23F2N3O5 m/z 380.3 (M+H)$^+$.

Step 7: Preparation of (R)-5-(5-aminomethyl-2-oxo-oxazolidin-3-yl)-7-fluoro-1-(2-fluoro-ethyl)-1,3-dihydro-indol-2-one (S)-{3-[7-Fluoro-1-(2-fluoro-ethyl)-2-oxo-2,3-dihydro-1H-indol-5-yl]-2-oxo-oxazolidin-5-ylmethyl}-carbamic acid tert-butyl ester (Step 6, 0.15 g, 0.395 mmol) is treated with 50% TFA/DCM (3 ml) for 15 minutes at room temperature. The reaction is evaporated and the title compound isolated as the TFA salt. HPLC r.t. 2.86 min; MS for C14H15F2N3O3 m/z 280.0 (M+H)$^+$.

Step 8: Preparation of (S)-{3-[7-fluoro-1-(2-fluoro-ethyl)-2-oxo-2,3-dihydro-1H-indol-5-yl]-2-oxo-oxazolidin-5-ylmethyl}-carbamic acid methyl ester Methyl chloroformate (0.022 ml, 0.282 mmol) is added dropwise to (R)-5-(5-aminomethyl-2-oxo-oxazolidin-3-yl)-7-fluoro-1-(2-fluoro-ethyl)-1,3-dihydro-iridol-2-one (0.080 g, 0.188 mmol) and diisopropylethylamine (0.137 ml, 0.752 mmol) in dichloromethane (2 ml) at 0° C. The reaction is stirred at 0° C. for 30 minutes and then allowed to warm at room temperature. The reaction mixture is diluted with dichloromethane, washed with water and brine, dried (Na$_2$SO$_4$) and evaporated. The residue is purified by PTLC (5% MeOH/DCM) to give the title compound as an off white solid. HPLC r.t. 3.93 min; $^1$H NMR (300 MHz, CDCl$_3$) 7.32 (m, 1H), 7.25 (m, 1H), 5.15 (m, 1H), 4.77 (m, 1H), 4.75 (t, J=5.1 Hz, 1H), 4.57 (t, J=4.8 Hz, 1H), 4.22 (t, J=5.1 Hz, 1H), 4.14 (t, J=4.8 Hz, 1H), 4.02 (t, J=9 Hz, 2H), 3.80 (dd, J=6.6, 9 Hz, 1H), 3.69 (s, 3H), 3.61 (s, 2H), 3.50-3.69 (m, 2H); MS for C$_{16}$H$_{17}$F$_2$N$_3$O$_5$ m/z 370.0 (M+H)$^+$.

EXAMPLE 5

Preparation of (S)-[3-(7-fluoro-2-oxo-1-propyl-2,3-dihydro-1H-indol-5-yl)-2-oxo-oxazolidin-5-ylmethyl]-carbamic acid methyl ester

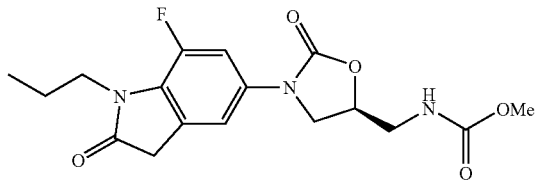

Step 1: Preparation of 7-fluoro-5-nitro-1-propyl-1,3-dihydro-indol-2-one

Crude (2,3-difluoro-5-nitrophenyl) acetic acid (2.00 g, 9.2 mmol) and n-propylamine (6 eq., 4.54 ml, 0.0553 mol) are mixed in DMSO (10 ml) and stirred at 50° C. for 2 hours. 2N Hydrochloric acid (40 ml) is added in one portion and the mixture stirred at room temperature for 2 hours. The resulting light yellow precipitate is filtered, washed with water and dried under vacuum. The residue is purified by flash column chromatography (20% Ethylacetate/hexane) to give the title compound as a yellow solid. HPLC r.t. 5.40 min; MS for C11H11FN2O3 m/z 239.1 (M+H)$^+$.

Step 2: Preparation of 5-amino-7-fluoro-1-propyl-1,3-dihydro-indol-2-one

Iron powder (0.855 g, 15.3 mmol) is added in small portions to 7-fluoro-5-nitro-1-propyl-1,3-dihydro-indol-2-one (0.910 g, 3.82 mmol) and ammonium chloride (2.02 g, 38.2 mmol) in ethanol (60 ml) and water (30 ml) at 90° C. The reaction mixture is stirred vigorously and heated for 60 min, cooled to room temperature, and diluted with dichloromethane (300 ml). The mixture is filtered through celite, the organic layer separated and washed with water and brine, dried over sodium sulfate and evaporated to give the title compound as a dark brown solid. HPLC r.t. 3.03 min; MS for C11H13FN2O m/z 209.0 (M+H)$^+$.

Step 3: Preparation of (R)-3-(7-fluoro-2-oxo-1-propyl-2,3-dihydro-1H-indol-5-ylamino)-2-hydroxy-propionic acid methyl ester 5-Amino-7-fluoro-1-propyl-1,3-dihydro-indol-2-one (0.300 g, 1.44 mmol), methyl (2R)-glycidate (0.147 g, 1.44 mmol) and lithium trifluoromethanesulfonate (0.220 g, 1.44 mmol) in acetonitrile (5 ml) are heated at 90° C. for 8 hours. The reaction is diluted with ethyl acetate, washed with water and brine, dried (Na$_2$SO$_4$) and evaporated. The residue is purified by PTLC (5% methanol/dichloromethane) to give the title compound as a yellow solid. HPLC r.t. 4.03 min; MS for C15H19FN2O4 m/z 311.2 (M+H)$^+$.

Step 4: Preparation of (R)-[3-(7-fluoro-2-oxo-1-propyl-2,3-dihydro-1H-indol-5-ylamino)-2-hydroxy-propyl]-carbamic acid tert-butyl ester 5-Amino-7-fluoro-1-propyl-1,3-dihydro-indol-2-one (0.500 g, 2.40 mmol), (S)-oxiranylmethyl-carbamic acid tert-butyl ester (0.417 g, 2.40 mmol) and lithium trifluoromethanesulfonate (0.368 g, 2.40 mmol) in acetonitrile (8 ml) are heated at 90° C. for 8 hours. The reaction mixture is diluted with ethyl acetate, washed with water and brine, dried (Na$_2$SO$_4$) and evaporated. Final purification by flash chromatography (70% Ethyl acetate/hexane) gives the title compound as a yellow solid. HPLC r.t. 4.30 min; MS for C19H28FN3O4 m/z 382.3 (M+H)$^+$.

Step 5: (S)-[3-(7-Fluoro-2-oxo-1-propyl-2,3-dihydro-1H-indol-5-yl)-2-oxo-oxazolidin-5-ylmethyl]-carbamic acid tert-butyl ester Phosgene (20% solution in toluene, 0.770 ml, 7.86 mmol) is added to (R)-[3-(7-fluoro-2-oxo-1-propyl-2,3-dihydro-1H-indol-5-ylamino)-2-hydroxy-propyl]-carbamic acid tert-butyl ester (0.400 g, 1.05 mmol) and triethylamine (0.726 ml, 5.24 mmol) in dichloromethane (5 ml) at 0° C. and stirred for 30 minutes. The mixture is diluted with dichloromethane, washed with water and brine, dried (Na$_2$SO$_4$) and evaporated to give the title compound as a dark yellow solid. HPLC r.t. 5.28 min; MS for C20H26FN3O5 m/z 408.1 (M+H)$^+$.

Step 6: Preparation of (R)-5-(5-aminomethyl-2-oxo-oxazolidin-3-yl)-7-fluoro-1-propyl-1,3-dihydro-indol-2-one (S)-[3-(7-Fluoro-2-oxo-1-propyl-2,3-dihydro-1H-indol-5-yl)-2-oxo-oxazolidin-5-ylmethyl]-carbamic acid tert-butyl ester (0.20 g, 0.491 mmol) is treated with 50% TFA/DCM (4 ml) for 15 minutes at room temperature. The reaction is evaporated and the title compound isolated as the TFA salt. HPLC r.t. 3.43 min; MS for C15H18FN3O3 Mol. Wt.: 307.32 m/z 308.0 (M+H)$^+$.

Step 7: Preparation of (S)-[3-(7-fluoro-2-oxo-1-propyl-2,3-dihydro-1H-indol-5-yl)-2-oxo-oxazolidin-5-ylmethyl]-carbamic acid methyl ester Methyl chloroformate (0.038 ml, 0.480 mmol) is added dropwise to (R)-5-(5-aminomethyl-2-oxo-oxazolidin-3-yl)-7-fluoro-1-propyl-1,3-dihydro-indol-2-one (0.135 g, 0.320 mmol) and diisopropylethylamine (0.235 ml, 1.28 mmol) in dichloromethane (3 ml) at 0° C. The reaction is stirred at 0° C. for 30 minutes and then allowed to warm at room temperature. The reaction mixture is diluted with dichloromethane, washed with water and brine, dried (Na$_2$SO$_4$) and evaporated. The residue is purified by PTLC (5% MeOH/DCM) to give the title compound as an off white solid. HPLC r.t. 4.40 min; $^1$H NMR (300 MHz, CDCl$_3$) 7.30 (m, 1H), 7.21 (m, 1H), 5.10 (t, 1H), 4.77 (m, 1H), 4.02 (t, J=9 Hz, 1H), 3.77-3.82 (m, 3H), 3.68 (s, 3H), 3.57 (s, 2H), 3.49-3.63 (m, 2H), 1.69 (m, 2H), 0.95 (t, J=7.5 Hz, 3H); MS for C$_{17}$H$_{20}$F$_2$N$_3$O$_5$ m/z 366.1 (M+H)$^+$.

EXAMPLE 6

Preparation of (S)-[3-(1-cyclopropyl-7-fluoro-2-oxo-2,3-dihydro-1H-indol-5-yl)-2-oxo-oxazolidin-5-ylmethyl]-carbamic acid methyl ester

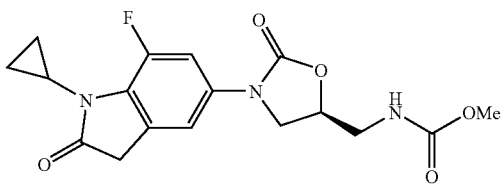

Step 1: Preparation of 1-cyclopropyl-7-fluoro-5-nitro-1,3-dihydro-indol-2-one Crude (2,3-difluoro-5-nitrophenyl) acetic acid (2.50 g, 11.5 mmol) and cyclopropylamine (6 eq., 4.78 ml, 0.0691 mol) are mixed in DMSO (10 ml) and stirred at 50° C. for 20 hours. 2N Hydrochloric acid (40 ml) is added in one portion and the mixture stirred at room temperature for 2 hours. The resulting light yellow precipitate is filtered, washed with water and dried under vacuum. The residue is purified by flash column chromatography (20% Ethyl acetate/hexane) to give the title compound as a yellow solid. HPLC r.t. 4.90 min; MS for $C_{11}H_9FN_2O_3$ m/z 235.0 $(M-H)^-$.

Step 2: Preparation of 5-amino-1-cyclopropyl-7-fluoro-1,3-dihydro-indol-2-one Iron powder (0.994 g, 17.8 mmol) is added in small portions to 1-cyclopropyl-7-fluoro-5-nitro-1,3-dihydro-indol-2-one (1.05 g, 4.44 mmol) and ammonium chloride (2.32 g, 44.5 mmol) in ethanol (50 ml) and water (25 ml) at 90° C. The reaction mixture is stirred vigorously and heated for 60 min, cooled to room temperature, and diluted with dichloromethane (250 ml). The mixture is filtered through celite, the organic layer separated and washed with water and brine, dried over sodium sulfate and evaporated to give the title compound as a yellowish-brown solid. HPLC r.t. 2.62 min; MS for $C_{11}H_{11}FN_2O$ m/z 207.2 $(M+H)^+$.

Step 3: Preparation of (R)-[3-(1-cyclopropyl-7-fluoro-2-oxo-2,3-dihydro-1H-indol-5-ylamino)-2-hydroxy-propyl]-carbamic acid tert-butyl ester 5-Amino-1-cyclopropyl-7-fluoro-1,3-dihydro-indol-2-one (0.560 g, 2.72 mmol), (S)-oxiranylmethyl-carbamic acid tert-butyl ester (0.472 g, 2.72 mmol) and lithium trifluoromethanesulfonate (0.415 g, 2.72 mmol) in acetonitrile (5 ml) are heated at 85° C. for 4.5 hours. The reaction mixture is diluted with ethyl acetate, washed with water and brine, dried ($Na_2SO_4$) and evaporated. Final purification by flash chromatography (70% Ethyl acetate/hexane) gives the title compound as a yellow solid. HPLC r.t. 3.98 min; MS for $C_{19}H_{26}FN_3O_4$ m/z 380.1 $(M+H)^+$.

Step 4: Preparation of (S)-[3-(1-cyclopropyl-7-fluoro-2-oxo-2,3-dihydro-1H-indol-5-yl)-2-oxo-oxazolidin-5-ylmethyl]-carbamic acid tert-butyl ester Phosgene (20% solution in toluene, 0.754 ml, 7.71 mmol) is added to (R)-[3-(1-cyclopropyl-7-fluoro-2-oxo-2,3-dihydro-1H-indol-5-ylamino)-2-hydroxy-propyl]-carbamic acid tert-butyl ester (0.390 g, 1.03 mmol) and triethylamine (0.711 ml, 5.13 mmol) in dichloromethane (5 ml) at 0° C. and stirred for 30 minutes. The mixture is diluted with dichloromethane, washed with water and brine, dried ($Na_2SO_4$) and evaporated to give the title compound as a yellow solid. HPLC r.t. 4.96 min; MS for $C_{20}H_{24}FN_3O_5$ m/z 406 $(M+H)^+$.

Step 5: Preparation of (R)-5-(5-aminomethyl-2-oxo-oxazolidin-3-yl)-1-cyclopropyl-7-fluoro-1,3-dihydro-indol-2-one (S)-[3-(1-Cyclopropyl-7-fluoro-2-oxo-2,3-dihydro-1H-indol-5-yl)-2-oxo-oxazolidin-5-ylmethyl]-carbamic acid tert-butyl ester (0.20 g, 0.493 mmol) is treated with 50% TFA/DCM (4 ml) for 15 minutes at room temperature. The reaction is evaporated and title compound isolated as the TFA salt. HPLC r.t. 3.17 min; MS for $C_{15}H_{16}FN_3O_3$ m/z 306.3 $(M+H)^+$.

Step 6: Preparation of (S)-[3-(1-cyclopropyl-7-fluoro-2-oxo-2,3-dihydro-1H-indol-5-yl)-2-oxo-oxazolidin-5-ylmethyl]-carbamic acid methyl ester Methyl chloroformate (0.055 ml, 0.715 mmol) is added dropwise to (R)-5-(5-aminomethyl-2-oxo-oxazolidin-3-yl)-1-cyclopropyl-7-fluoro-1,3-dihydro-indol-2-one (Example 50, Step 5, 0.200 g, 0.476 mmol) and diisopropylethylamine (0.349 ml, 1.90 mmol) in dichloromethane (5 ml) at 0° C. The reaction is stirred at 0° C. for 30 minutes and then allowed to warm at room temperature. The reaction mixture is diluted with dichloromethane, washed with water and brine, dried ($Na_2SO_4$) and evaporated. The residue is purified by PTLC (5% MeOH/DCM) to give the title compound as a yellow solid. HPLC r.t. 4.05 min; $^1$H NMR (300 MHz, $CDCl_3$) 7.23 (m, 1H), 7.18 (m, 1H), 5.12 (t, 1H), 4.77 (m, 1H), 4.02 (t, J=8.7 Hz, 1H), 3.79 (dd, J=6.6, 9 Hz, 1H), 3.69 (s, 3H), 3.51 (m, 2H), 2.85 (m, 1H), 0.97 (m, 2H); MS for $C_{17}H_{18}FN_3O_5$ m/z 364.0 $(M+H)^+$.

EXAMPLE 7

Preparation of (S)-[3-(1-cyclopropylmethyl-7-fluoro-2-oxo-2,3-dihydro-1H-indol-5-yl)-2-oxo-oxazolidin-5-ylmethyl]-carbamic acid methyl ester

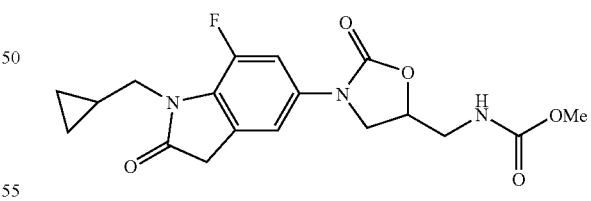

Step 1: 1-Cyclopropylmethyl-7-fluoro-5-nitro-1,3-dihydro-indol-2-one

Crude (2,3-difluoro-5-nitrophenyl) acetic acid (2.50 g, 11.5 mmol) and (aminomethyl)cyclopropane (6 eq., 5.98 ml, 0.0691 mol) are mixed in DMSO (10 ml) and stirred at 45° C. for 20 hours. 2N Hydrochloric acid (40 ml) is added in one portion and the mixture stirred at room temperature for 2 hours. The resulting light yellow precipitate is filtered, washed with water and ether, and dried under vacuum to give the title compound as a yellow solid. HPLC r.t. 4.91 min; MS for C12H11FN2O3 m/z 251.2 (M+H)⁺.

Step 2: Preparation of 5-amino-1-cyclopropylmethyl-7-fluoro-1,3-dihydro-indol-2-one Iron powder (0.995 g, 18.1 mmol) is added in small portion to a mixture of 1-methyl-5-nitro-1,3-dihydro-indol-2-one (1.00 g, 4.52 mmol) and ammonium chloride (2.40 g, 45.2 mmol) in ethanol (20 ml) and water (10 ml) at 90° C. The reaction mixture is stirred vigorously and heated for 60 minutes, cooled to room temperature, and diluted with dichloromethane (100 ml). The mixture is filtered through celite, the organic layer separated and washed with water and brine, dried over sodium sulfate, and evaporated to give the title compound as a dark brown solid. HPLC r.t. 3.13 min; MS for C16H18FN3O3 m/z 221.0 (M+H)⁺.

Step 3: Preparation of (R)-[3-(1-cyclopropylmethyl-7-fluoro-2-oxo-2,3-dihydro-1H-indol-5-ylamino)-2-hydroxy-propyl]-carbamic acid tert-butyl ester 5-Amino-1-cyclopropylmethyl-7-fluoro-1,3-dihydro-indol-2-one (1.00 g, 4.55 mmol), (S)-oxiranylmethyl-carbamic acid tert-butyl ester (0.79 g, 4.55 mmol) and lithium trifluoromethanesulfonate (0.618 g, 4.55 mmol) in acetonitrile (20 ml) are heated at 90° C. for 16 hours. The reaction mixture is diluted with ethyl acetate, washed with water and brine, dried (Na₂SO₄) and evaporated. Final purification by flash chromatography (70% ethyl acetate/hexane) gives the title compound as a white solid. HPLC r.t. 4.35 min; MS for C20H28FN3O4 m/z 394.1 (M+H)⁺.

Step 4: Preparation of (S)-[3-(1-cyclopropylmethyl-7-fluoro-2-oxo-2,3-dihydro-1H-indol-5-yl)-2-oxo-oxazolidin-5-ylmethyl]-carbamic acid tert-butyl ester Phosgene (20% solution in toluene, 1.50 ml, 14.1 mmol) is added to (R)-[3-(1-cyclopropylmethyl-7-fluoro-2-oxo-2,3-dihydro-1H-indol-5-ylamino)-2-hydroxy-propyl]-carbamic acid tert-butyl ester (0.74 g, 1.88 mmol) and triethylamine (0.95 ml, 9.41 mmol) in dichloromethane (15 ml) at 0° C. and then stirred at 0° C. for 20 minutes. The mixture is diluted with dichloromethane, washed with water and brine, dried (Na₂SO₄) and evaporated. The residue is purified by flash column chromatography (70% ethyl acetate/hexane) to give the title compound as a white solid. HPLC r.t. 5.39 min; MS for C21H26FN3O5 m/z 420.1 (M+H)⁺.

Step 5: Preparation of (R)-5-(5-aminomethyl-2-oxo-oxazolidin-3-yl)-1-cyclopropylmethyl-7-fluoro-1,3-dihydro-indol-2-one (S)-[3-(1-Cyclopropylmethyl-7-fluoro-2-oxo-2,3-dihydro-1H-indol-5-yl)-2-oxo-oxazolidin-5-ylmethyl]-carbamic acid tert-butyl ester (0.48 g, 1.14 mmol) is treated with 50% TFA/DCM (10 ml) for 60 minutes at room temperature. The reaction is evaporated and the title compound isolated as the TFA salt. HPLC r.t. 3.61 min; MS for C16H18FN3O3 m/z 320.3 (M+H)⁺.

Step 6: Preparation of (S)-[3-(1-cyclopropyl-7-fluoro-2-oxo-2,3-dihydro-1H-indol-5-yl)-2-oxo-oxazolidin-5-ylmethyl]-carbamic acid methyl ester Methyl chloroformate (0.070 ml, 0.858 mmol) is added dropwise to (R)-5-(5-aminomethyl-2-oxo-oxazolidin-3-yl)-1-cyclopropylmethyl-7-fluoro-1,3-dihydro-indol-2-one (0.300 g, 0.709 mmol) and diisopropylethylamine (0.37 ml, 2.13 mmol) in dichloromethane (15 ml) at 0° C. The reaction is stirred at 0° C. for 30 minutes and then allowed to warm at room temperature. The reaction mixture is diluted with dichloromethane, washed with water and brine, dried (Na₂SO₄) and evaporated. The residue is purified by PTLC (10% MeOH/DCM) to give the title compound as an off white solid. HPLC r.t. 4.55 min; ¹H NMR (300 MHz, CDCl3) 7.52 (1H), 7.39 (s, H), 7.35 (s, 1H), 4.68-4.66 (m, 1H), 4.09 (t, J=9.0 Hz, 1H), 3.74 (dd, J=9, 6 Hz, 1H), 3.69 (s, 2H), 3.59 (d, J=7.2 Hz, 2H), 3.53 (s, 3H), 3.33 (t, J=5.4 Hz, 2H), 1.26-1.23 (m, 1H), 0.47-0.42 (m, 2H), 0.32-0.29 (m, 2H); MS for C18H20FN3O5 m/z 378.1(M+H)⁺.

The invention claimed is:

1. A compound of formula I

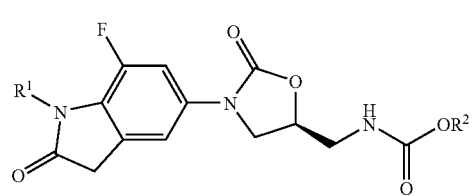

or a pharmaceutically acceptable salt thereof wherein R¹ is C₁₋₄alkyl, optionally substituted with a fluoro atom, or R¹ is a cyclopropyl or cyclopropylmethyl; and R² is methyl or ethyl.

2. A compound of claim 1 wherein R² is methyl.

3. A compound of claim 2 wherein R¹ is methyl.

4. A compound of claim 2 wherein R¹ is isopropyl.

5. A compound of claim 2 wherein R¹ is ethyl, fluoroethyl, propyl, cyclopropyl, or cyclopropylmethyl.

6. A pharmaceutical composition comprising a compound of claim 1 or a pharmaceutically acceptable salt thereof, and a pharmaceutically acceptable carrier.

7. A method for treating bacteria infections comprising administering to a mammal being treated a pharmaceutically effective amount of the compound of claim 1.

8. The method of claim 7 wherein the compound of claim 1 is administered orally.

9. The method of claim 7 wherein the compound of claim 1 is administered parenterally topically, rectally or intranasally.

10. The method of claim 7 wherein said compound is administered in an amount of from about 0.1 to about 100 mg/kg of body weight/day.

11. The method of claim 7 wherein said compound is administered in an amount of from about 1 to about 50 mg/kg of body weight/day.

12. The bacteria infection of claim 7 which is ear infections, eye infections, respiratory tract infections, skin and skin structure infections, bacterial endocarditis, osteomyelitis endocarditis or diabetic foot.

13. The bacteria infection of claim 7 which is caused by gram-positive bacteria, gram negative bacteria, anaerobic organisms, and acid-fast organisms.

14. The bacteria infection of claim 7 which is caused by bacteria comprising *staphylococci, streptococci, Enterococci, Haemophilus, Moraxella*, bacterioides, *clostridia, Mycobacteria*, or *Chlamydia*.

15. The bacteria of claim 14 wherein staphylococci is *S. aureus* and *S. epidermidis;* wherein streptococci is *S. pneumoniae* of *S. pyogenes;* wherein Enterococci is *E. faecalis;* wherein *Haemophilus* is *H. influenzae;* wherein *Moraxella* is *M. catarrhalis;* and wherein *Mycobacteria* is *M. tuberculosis;* or *Mycobacterium avium.*

16. The bacteria infections of claim 7 which is caused by multi-drug resistant *S. aureus.*

17. A compound of claim 1 which is (5S)-[3-(7-fluoro-1-methyl-2-oxo-2,3-dihydro-1H-indol-5-yl)-2-oxo-oxazolidin-5-ylmethyl]-carbamic acid methyl ester.

18. The compound of claim 17 wherein said compound is substantially free of its opposite enantiomer.

19. The compound of claim 17 wherein said compound is in at least 90% enantiomeric excess.

\* \* \* \* \*